United States Patent [19]

Ezekwe et al.

[11] Patent Number: 5,688,508

[45] Date of Patent: Nov. 18, 1997

[54] FEED COMPOSITIONS COMPRISING PURSLANE LEAVES AND METHODS OF USING THEREOF

[75] Inventors: Michael O. Ezekwe, Colonial Heights; Thomas R. Omara-Alwala, Chester; Tadesse Mebrahtu, Prince George, all of Va.

[73] Assignee: Virginia State University, Petersburg, Va.

[21] Appl. No.: 391,188

[22] Filed: Feb. 21, 1995

[51] Int. Cl.⁶ .......... A01N 63/00; A01N 65/00; A23K 1/18; C12N 5/00

[52] U.S. Cl. ........ 424/195.1; 424/93.7; 424/93.73; 426/2; 426/807; 426/809; 435/240.4

[58] Field of Search ............. 424/93.7, 93.73, 424/195.1; 426/2, 807, 809; 435/240.4

[56] References Cited

U.S. PATENT DOCUMENTS 5,133,963  7/1992  Ise .......................... 424/94.61

OTHER PUBLICATIONS

Jirovetz *et al.*, Ernahrung, 1993, see abstr.

Omara–Alwala *et al.*, J. of Amer. Oil Chemists' Soc., 1991, see abstr.

Ranhotra *et al.*, Cereal Chemistry, 1992, see abstr.

*Primary Examiner*—John W. Rollins
*Assistant Examiner*—Deborah K. Ware
*Attorney, Agent, or Firm*—Birch, Stewart, Kolasch & Birch, LLP

[57] ABSTRACT

The present invention is drawn to feed compositions including purslane leaves harvested at bloom. The present invention is further drawn to methods of reducing serum cholesterol and triglycerides with the present feed compositions of purslane leaves, as well as methods of preventing and treating coronary heart disease with the feed compositions.

8 Claims, 3 Drawing Sheets

FEED COMPOSITIONS COMPRISING PURSLANE LEAVES AND METHODS OF USING THEREOF

BACKGROUND OF THE INVENTION

The present invention relates to the process of reducing plasma cholesterol and triglycerides by the use of a naturally-occurring component of purslane (genus, portulaca). This invention pertains to the U.S. Utility Patent Classification definition.

Sixty million Americans have elevated blood cholesterol levels which, in combination with other risk factors e.g. high triglyceride levels, place them at risk of coronary heart disease (Inform, Dietary fat: New directions in research AOCS 1:238–260 (1990)). In view of the fact that Omega-3 fatty acids have been associated with decreasing mortality from coronary artery disease, it has become necessary to identify sources of Omega-3 fatty acids in the food supply. Recent reports indicate that reduction in plasma cholesterol in high risk groups is associated with more lives saved.

Purslane, a ubiquitous garden weed in the U.S., is the richest vegetable source of Omega-3 fatty acids (Simopoulos et al., Purslane: A terrestrial source of Omega-3 fatty acids, New England J. 315(13):833 (1986); Simopoulos et al., Common Purslane: A source of Omega-3 fatty acids and antioxidants. J. Am. Coll. Nutr. 11:374–382 (1992); Omara-Alwala et al., Omega-3 fatty acids in purslane (Portulaca oleracea) tissue, J. Am. Oil Chem. Soc. 68:198–199 (1991)). Although Omega-3 fatty acids lower serum cholesterol and triglycerides and consequently reduce the incidence of cardiovascular diseases in human, no one has yet demonstrated this using purslane plant.

SUMMARY OF THE INVENTION

One object of the present invention is drawn to a feed composition comprising purslane leaves wherein said purslane leaves have been harvested from a plant at full bloom.

An additional object of the present invention is drawn to methods of reducing serum cholesterol and triglycerides using the present feed compositions.

Another object of the present invention encompasses methods of treating or preventing coronary heart disease using the present feed compositions.

DETAILED DESCRIPTION OF THE INVENTION

Figure 1:
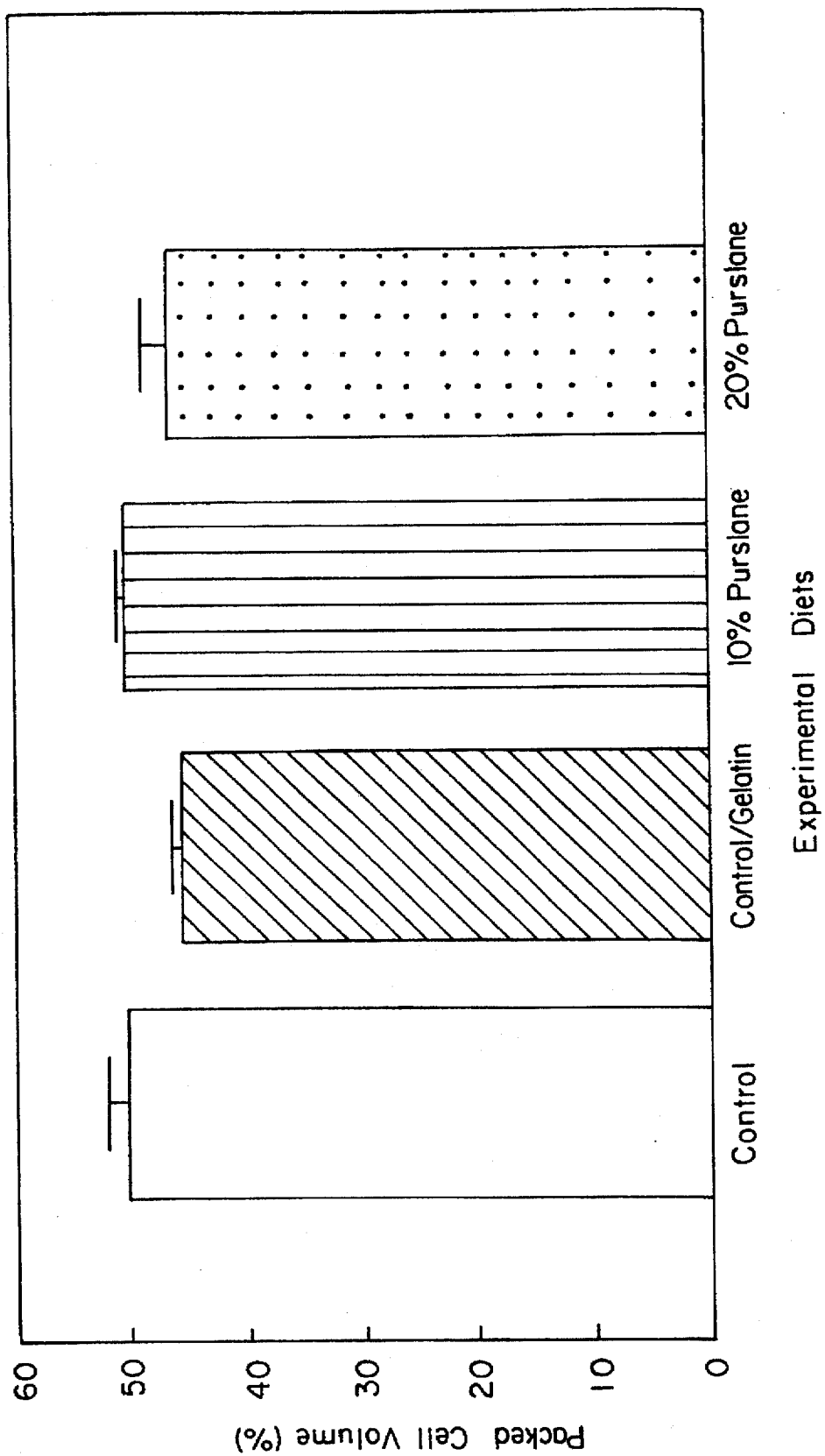
FIG. 1 illustrates graphically blood hematocrit levels in rats fed purslane leaf supplement added to basal commercial diet at a rate of 0, 10 and 20% of the diet.

In order to demonstrate that purslane can reduce plasma cholesterol and/or triglycerides, it is necessary to present the ingredient in a form that preserves constituents to an animal species with close physiological similarities to humans.

The present invention is drawn to feed compositions comprising purslane leaves harvested at full bloom and to methods of reducing serum cholesterol and triglycerides, as well as treating and preventing coronary heart disease using the present feed compositions.

Seeds of purslane genotypes were received from various geographical locations and planted at Virginia State University Randolph Farm during the 1993 growing season. Purslane plants harvested at bloom from the field were frozen after harvesting. Leaves were later removed and lyophilized overnight in a freeze dryer Model Labconco Lyph. Lock 12. Lyophilized leaves from all the genotypes were pooled and analyzed for proximate composition. Leaf powder was formed by smashing the freed dried leaves collected in a plastic bag. Commercial rat chow containing 18 and 8% crude protein and fat (guaranteed analysis), respectively, was used as a basal diet and supplemented with either 10 or 20% total weight freeze-dried purslane leaf powder. The commercial chow was ground and mixed with two levels of purslane, and cotton seed oil was added to formulate an iso-nitrogenous diet with similar lipid caloric content. A third diet contained gelatin only which was used as a binder for all the experimental diet. The commercial diet served as the control The mixture containing 4% gelatin as a binding agent was repelleted into cubes and dried.

Female Sprague Dawley rats (Camm Laboratories, Wayne, N.J.) were housed in individual cages in a room with 12-h light: dark cycle. The animals were fed the commercial stock diet ad libitum, during a 2-week acclimation period. Twenty-four 7–8 week-old rats, stratified by body weight, were assigned to one of four diet groups (Table 1) and fed ad libitum for 6 weeks.

Feed intake and body weight measurements were taken weekly. At the end of the feeding trial, the rats were fasted for 24 hours before sacrifice. Animals were mechanically stunned, followed by exsanguination. At sacrifice, blood was collected and used for blood hematocrit determination (Henry, Clinical diagnosis and management by laboratory methods, W. B. Saunders Co., Philadelphia, Pa. (1984)). Blood plasma was used for biochemical determinations of cholesterol and triglycerides (Stanbio Laboratories, Inc, San Antonio, Tex.). Liver, kidney (left) and gastrocnemius muscles (left leg) were dissected out and weighed. Liver and muscle tissue were used for chemical determinations. Body composition and feed proximate analyses were determined by the AOAC methods (AOAC, Official methods of analysis, Association of Official Agricultural Chemists, Arlington, Va. (1990)). The data were analyzed by a one-way analysis of variance. Means were separated by LSD technique at 5% level of significance (Steel and Torrie, Principles and procedures of statistics, McGraw-Hill, New York N.Y. (1980)).

RESULTS AND DISCUSSION

Figure 2:
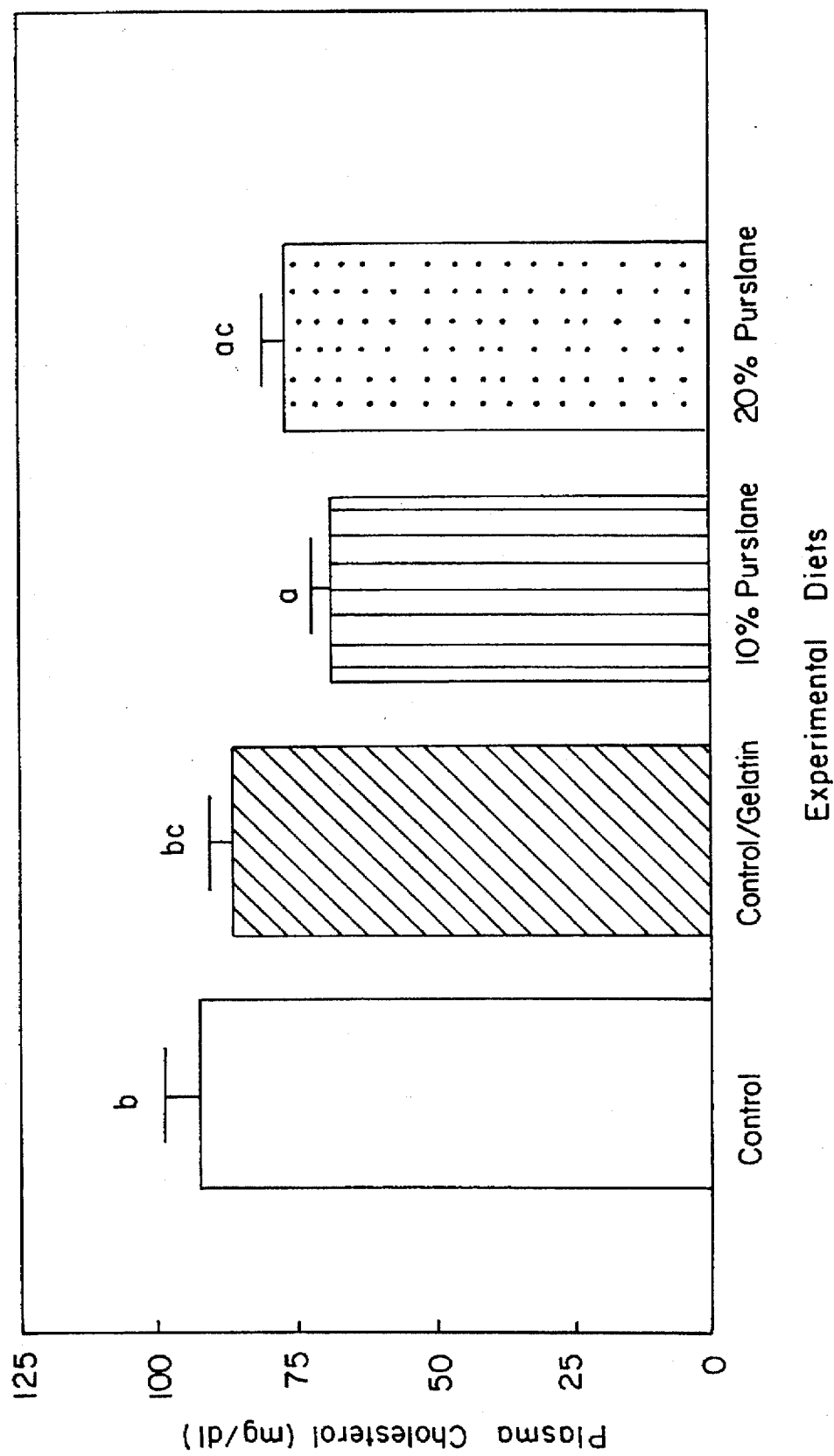
FIG. 2 illustrates graphically plasma cholesterol levels in rats fed purslane leaf supplement added to a basal commercial diet at a rate of 0, 10 and 20% of the diet. Values not sharing a superscript are statistically different at 5% level of probability.
Figure 3:
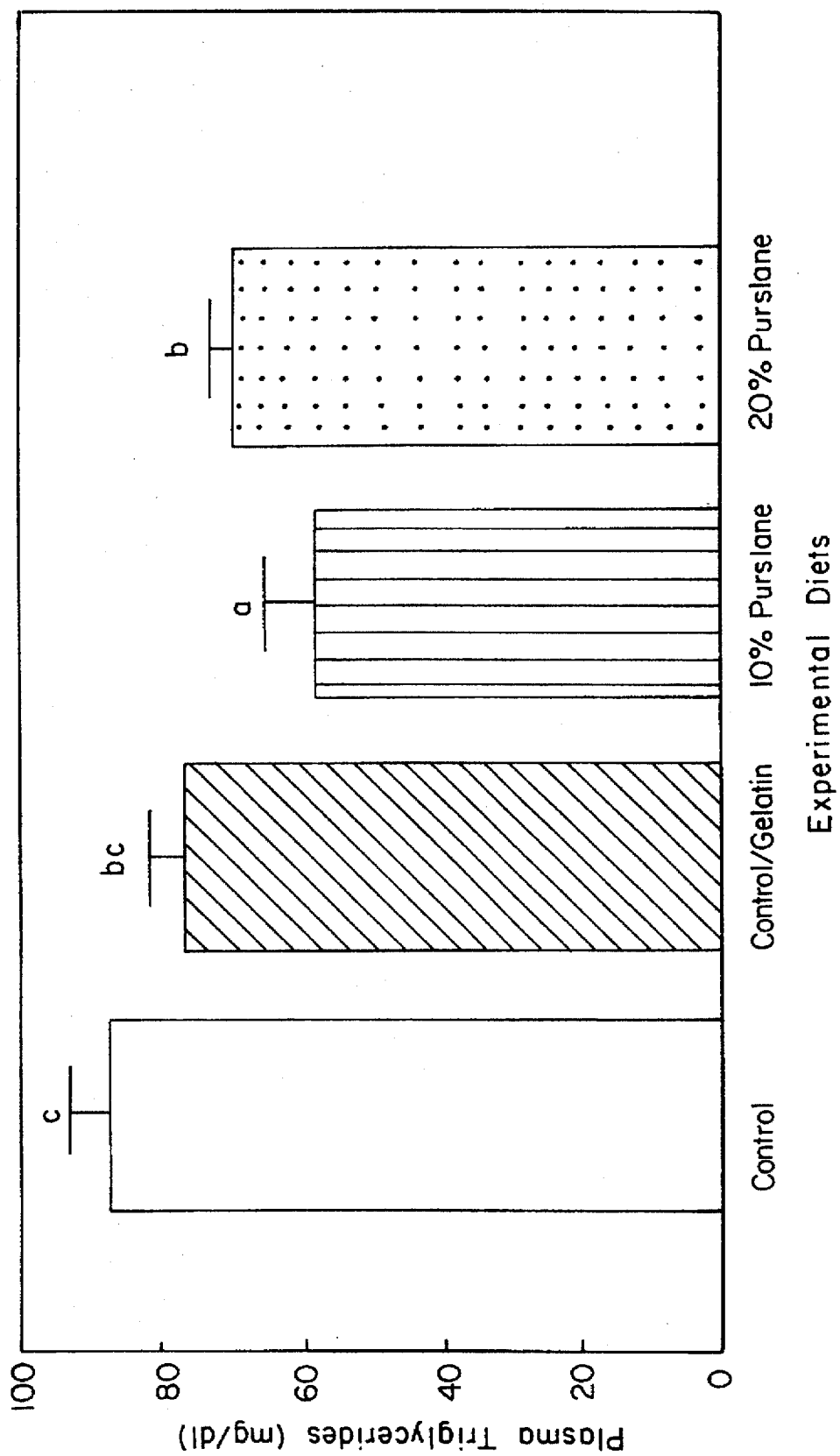
FIG. 3 illustrates graphically plasma triglycerides levels in rats fed purslane leaf supplement added to a basal commercial diet at a rate of 0, 10 and 20% of the diet. Values not sharing a superscript are statistically different at 5% level of probability.

The hematocrit response to purslane supplements is presented in FIG. 1. There was no difference ($P>0.05$) in packed cell volume of the blood among treatments. Total plasma cholesterol and triglyceride levels were significantly ($P<0.05$) reduced in rats consuming 10 and 20% purslane diets (FIGS. 2 and 3). Total plasma cholesterol levels were reduced by 26 and 17% in rats receiving 10 and 20% purslane diets, respectively, compared with those of the control. Gelatin addition to control diet reduced cholesterol levels by 7%, suggesting a caloric density dilution due to gelatin. The net reductions in cholesterol due to purslane were 19 and 10% in 10 and 20% putslane diets, respectively. Maximal cholesterol reduction was achieved at 10% level of purslane supplementation. The response of rats to the 20% level of purslane could have been influenced by protein quality which is unknown.

A similar response was observed in plasma triglycerides. A significant reduction ($P<0.05$) in plasma triglycerides noted in the rats receiving 10% and 20% purslane indicated a potent hypotriglyceridemic effect of purslane. Significant differences were observed between the triglyceride levels of rats in the 10 and 20% levels of supplementation. There were 33 and 20% reductions in triglyceride levels of rats consuming 10 and 20% purslane diets, respectively, compared with those of the control. A 12% reduction attributable to gelatin suggests that net values of 21 and 18% of plasma triglycerides were due to 10 and 20% purslane diets, respectively.

This is the first study of its kind establishing the nutritional benefits of purslane in an animal species.

The high crude protein content of pooled purslane leaves (22.4%) noted in this study is in agreement with previous studies (Kabulov and Tashbekov, Purslane Kaftofel'i Ovoschi 8:45–46 (1979); Ezekwe et al., The influence of planting date on nutritive quality of purslane genotypes, FASEB J. 8:932A (1994)). This high crude protein value places purslane above alfalfa, generally considered as the most valued protein source for grazing animals. Alfalfa with 17% crude protein (NRC, National Research Council, Nutrient requirements of swine, National Academy Press, Washington, D.C. (1988)) is the most important commercial forage crop for animals in the United States. Purslane with over 100 species and known to be found in every region of the world has the potential for becoming a highly nutritious vegetable for both animals (fodder) and human consumption.

The growth and performance of the rats during experiments (Table 2) as well as the organ weights and composition (Table 3) showed similar trends in all treatments. No differences were observed in body weight gain, feed intake, organ weights and chemical composition ($P>0.05$). Although purslane diets tended to lower liver lipids, these differences were not significant.

Chemical body composition showed no differences among treatments (Table 4), agreeing well with performance data previously discussed (Table 2). It has been reported that purslane under certain conditions can accumulate large quantities of oxalates. However, Kesden and Will (Purslane, A ubiquitous garden weed with nutritional potential, Proc. Fla. State Hort. Soc. 100, 195–197 (1987)) have suggested that this excessive accumulation of oxalates does not appear to be a problem in North America. Similar growth response, body compositions, and organs of rats consuming both purslane and control diet indicate that purslane is quite safe at the level offered in this experiment. However, rats receiving 10% purslane supplements responded better than those on 20% diet. Gelatin dilution and possible amino acid balance of purslane protein could be factors in the performance of rats consuming 20% purslane.

TABLE 1

COMPOSITION OF EXPERIMENTAL DIETS[a]

| Item | Control g/100 g | Control/ Gelatin g/100 | 10% Purslane g/100 g | 20% Purslane g/100 |
|---|---|---|---|---|
| Basal Diet | 100.00 | 100.00 | 87.60 | 75.10 |
| Purslane | — | — | 10.00 | 20.00 |
| Cotton Seed Oil | — | — | .64 | 1.90 |
| Gelatin[b] | — | 4.00 | 1.76 | 3.00 |
| Total | 100 | 104 | 100 | 100 |
| Calculated Composition | | | | |
| Protein | 18 | 18 | 18 | 18 |
| Fat | 8 | 8 | 8 | 8 |

[a]Basal commercial diet contains 18% crude protein and 8% lipid. All diets were isonitrogenous and lipid isocaloric.
[b]Additional 4% gelatin was used as a binder in 10 and 20% purslane diets.

TABLE 2

BODY WEIGHT, FEED INTAKE, AND ADG IN RATS FED PURSLANE SUPPLEMENTS[a]

| Item[b] | Control | Control/ Gelatin | 10% Purslane | 20% Purslane |
|---|---|---|---|---|
| Initial body weight, g | 214.7 ± 5.9 | 213.3 ± 8.3 | 206.0 ± 6.0 | 209.0 ± 6.5 |
| Final body weight, g | 262.7 ± 9.2 | 258.7 ± 9.1 | 253.0 ± 5.7 | 249.3 ± 5.7 |
| Gain, g | 48.0 ± 6.3 | 45.3 ± 3.0 | 47.0 ± 2.5 | 40.3 ± 5.8 |
| ADG, g | 1.4 ± .2 | 1.2 ± .1 | 1.4 ± .1 | 1.2 ± .2 |
| Feed Intake, g | 609.3 ± 18.6 | 598.3 ± 24.9 | 611.2 ± 18.0 | 564 ± 8.9 |

[a]Means + SEM for 6 animals
[b]Did not differ ($P > 0.5$)

TABLE 3

LIVER, KIDNEY AND GASTROCNEMIUS MUSCLE WEIGHT, PROTEIN AND LIPID LEVELS IN RATS FED PURSLANE SUPPLEMENTS[a]

| Item[b] | Control | Control/ Gelatin | 10% Purslane | 20% Purslane |
|---|---|---|---|---|
| Liver weight, g | 6.7 ± .3 | 5.9 ± .3 | 6.2 ± .2 | 5.7 ± .2 |
| Kidney weight, g | .9 ± .02 | .9 ± .1 | .9 ± .04 | .8 ± .04 |
| Muscle weight, g | 1.7 ± .1 | 1.7 ± .1 | 1.7 ± .1 | 1.7 ± .03 |
| Liver protein, % | 22.4 ± .4 | 23.0 ± .2 | 22.9 ± .3 | 23.4 ± .4 |
| Liver lipids, % | 6.0 ± .3 | 6.3 ± .5 | 5.7 ± .2 | 5.5 ± .3 |
| Muscle protein, % | 22.1 ± .1 | 22.4 ± .2 | 22.0 ± .2 | 22.0 ± .1 |
| Muscle lipids, % | 2.1 ± .3 | 2.3 ± .3 | 1.9 ± .2 | 2.7 ± .3 |

[a]Means ± SEM for 6 animals
[b]Did not differ ($P > 0.5$)

TABLE 4

CARCASS WEIGHT AND CHEMICAL BODY COMPOSITION OF RATS FED PURSLANE SUPPLEMENTS[a]

| Item[b] | Experimental Diets | | | |
|---|---|---|---|---|
| | Control | Control/Gelatin | 10% Purslane | 20% Purslane |
| Carcass weight, g | 227.6 ± 7.0 | 215.6 ± 9.0 | 214.2 ± 5.9 | 208.6 ± 7.6 |
| Protein, % | 19.4 ± .4 | 20.1 ± .6 | 18.3 ± .8 | 18.7 ± .4 |
| Fat, % | 10.4 ± .5 | 9.6 ± .6 | 9.7 ± .5 | 9.9 ± .6 |
| Ash, % | 5.9 ± .7 | 4.9 ± .6 | 4.5 ± .5 | 4.9 ± .2 |
| Moisture, % | 56.1 ± 1.4 | 59.9 ± 1.1 | 60.5 ± .9 | 59.1 ± 1.3 |

[a]Means + SEM for 6 animals
[b]Did not differ (P > .05)

We claim:

1. A feed composition capable of reducing serum cholesterol and triglycerides comprising an effective amount of purslane leaves, wherein said leaves are obtained from purslane plants in full bloom.

2. The composition of claim 1, wherein said purslane leaves are present in an amount of 10% of the total weight of the composition.

3. The composition of claim 1, wherein said purslane leaves are present in an amount of 20% of the total weight of the composition.

4. A method of reducing serum cholesterol and triglycerides comprising feeding to an animal for a period of time an effective amount of a feed composition comprising at least 10% purslane leaves, wherein said leaves are obtained from purslane plants in full bloom.

5. The method of claim 4 wherein said animal is a human or a grazing animal.

6. A method of treating or preventing coronary heart disease comprising feeding to an animal for a period of time in an effective amount of a feed composition comprising at least 10% purslane leaves, wherein said leaves are obtained from purslane plants in full bloom.

7. The method of claim 6, wherein said animal is a human or a grazing animal.

8. The method of claim 4 or 6, wherein said feed composition is fed to said animal for at least six weeks.

* * * * *